United States Patent
Chen et al.

(10) Patent No.: US 8,309,626 B2
(45) Date of Patent: Nov. 13, 2012

(54) MICROBIOCIDAL COATINGS

(75) Inventors: Henry Huan Chen, Shanghai (CN); Jennifer Reichl Collin, Devon, PA (US); Lynn Carol Munz, Harleysville, PA (US); Christopher John Tucker, Midland, MI (US); Janet Nadya Younathan, Lansdale, PA (US); Yonnie Dong Yun, Shanghai (CN); Fanwen Zeng, Belle Mead, NJ (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/179,639

(22) Filed: Jul. 11, 2011

(65) Prior Publication Data

US 2012/0016055 A1 Jan. 19, 2012

(30) Foreign Application Priority Data

Jul. 13, 2010 (CN) .......................... 2010 1 0234638

(51) Int. Cl.
*C09D 5/16* (2006.01)
*C08K 5/13* (2006.01)
*C08K 3/28* (2006.01)
*C08K 5/34* (2006.01)

(52) U.S. Cl. ..................... 523/122; 427/385.5; 524/100; 524/186; 524/323; 524/428

(58) Field of Classification Search .................. 523/122; 427/385.5; 524/100, 323, 186, 428
See application file for complete search history.

(56) References Cited

U.S. PATENT DOCUMENTS

| | | | |
|---|---|---|---|
| 4,098,987 A | 7/1978 | Barua et al. | |
| 4,151,333 A | 4/1979 | Lenke | |
| 4,395,524 A | 7/1983 | Emmons | |
| 5,061,485 A | 10/1991 | Oakes | |
| 6,146,652 A | 11/2000 | Gore et al. | |
| 6,270,754 B1 | 8/2001 | Zhou | |
| 2002/0014178 A1* | 2/2002 | Haught et al. | 106/15.05 |
| 2003/0224030 A1 | 12/2003 | Uchiyama et al. | |
| 2004/0013638 A1 | 1/2004 | Aubay | |
| 2005/0009971 A1 | 1/2005 | Hodge et al. | |
| 2007/0166344 A1 | 7/2007 | Qu | |
| 2007/0219307 A1 | 9/2007 | Yang et al. | |
| 2008/0026026 A1 | 1/2008 | Lu | |
| 2009/0155451 A1 | 6/2009 | Ylitalo | |
| 2010/0081729 A1 | 4/2010 | Collin | |

FOREIGN PATENT DOCUMENTS

| | | |
|---|---|---|
| EP | 0194770 | 9/1986 |
| EP | 2161311 | 3/2010 |
| GB | 1553132 | 9/1979 |
| WO | 2004062363 | 7/2004 |
| WO | 2004100665 | 11/2004 |

OTHER PUBLICATIONS

Martin B. Hocking, "Water-soluble acrylamide copolymers. VIII. Preparation and characterization of polyacrylamide-co-N-t-butylacrylamide," J. Polymer Science Part A., vol. 39, p. 1960, 2001.

* cited by examiner

*Primary Examiner* — Kriellion Sanders
(74) *Attorney, Agent, or Firm* — Carl P. Hemenway; Tifani M. Edwards

(57) ABSTRACT

There is provided a coating composition comprising
(a) one or more microbicide,
(b) one or more soluble polymer comprising acrylamide as polymerized units, wherein said polymer has is non-anionic, and
(c) solvent, wherein said polymer is dissolved in said solvent. Also provided is a method of coating a substrate with such a coating, and also provided is the resulting coated substrate.

9 Claims, No Drawings

MICROBIOCIDAL COATINGS

BACKGROUND

It is often desirable to provide a surface on which microorganisms, many of which are potentially harmful, are inhibited from growing. Many useful materials have surfaces that do not normally inhibit the growth of microorganisms. One useful way to improve the microorganism inhibition of a surface is to coat that surface with a coating that provides a microorganism-inhibiting effect.

One common method of coating a surface is to apply a layer of a liquid coating composition to that surface and then dry the layer or allow the layer to dry. It is desirable that such liquid coating compositions are clear and remain stable during storage. It is also desirable that such liquid coating compositions spread evenly when applied to a hard, flat surface.

It is desirable that such coatings, when dry, have one or more of the following desirable properties: clarity; non-tackiness; durability; removability; and ability to maintain microorganism-inhibition under normal use for an extended period of time (for example, 24 hours or longer) after application to a surface.

One approach to providing a microorganism-inhibiting coating is disclosed by U.S. patent application Ser. No. 12/584,324, which describes coating compositions that contain microbicide, solvent, and polymer. The polymer described in U.S. patent application Ser. No. 12/584,324 contains, as polymerized units, one or more monomer with a pendant heterocycle. Such monomer can be expensive to manufacture and to purchase. It is desired to provide microbicidal coatings that have one or more of the above properties and that are made from monomers that include acrylamide.

STATEMENT OF THE INVENTION

There is provided a coating composition comprising
(a) one or more microbicide,
(b) one or more soluble polymer comprising acrylamide as polymerized units, wherein said polymer is a non-anionic polymer, and
(c) solvent,
wherein said polymer is dissolved in said solvent.

DETAILED DESCRIPTION

As used herein, the following terms have the designated definitions, unless the context clearly indicates otherwise. The term "microbicide", "biocide", "preservative" or "antimicrobial compound" refers to a compound capable of killing, inhibiting the growth of, or controlling the growth of microorganisms; microbicides include bactericides, fungicides, viricides and algicides. The term "microorganism" includes, for example, fungi (such as yeast and mold), bacteria, viruses and algae.

Microorganisms that are affected by microbicide include, but are not limited to, *Aureobasidium pullulans, Bacillus cereus, Bacillus thuringiensis, Chaetomium globosum, Enterobacter aerogines, Escherichia coli, Gliocladtum vixens, Klebsiella pneumoniae, Legionella pneumpophila, Listeria monocytogenes, Mycobacterium tuberculosis, Porphyromonas gingivalis, Proteus mirabilis, Proteus vulgaris, Pseudomonas aeruginosa, Saccharomyces cerevisiae, Salmonella gallinarum, Salmonella typhimurium, Staphylococcus aureus, Staphylococcus epidermidis, Streptococcus agalactiae, Streptococcus faecalis, Streptococcus mutans, Trycophyton malmsten, Vibrio parahaemolyticus, Stachybotrys, Aspergillus niger, Candida albicans, Penicillium funiculosum, Methicillin*-resistant *Staphylococcus aureus* (MRSA), and *Vancomycin*-resistant *enterococcus* (VRE).

Unless otherwise specified, temperatures discussed herein are in degrees centigrade (° C.), and references to percentages (%) are by weight.

Herein, "acid number" of a polymer is the milligrams of potassium hydroxide required to neutralize the acidic groups on that polymer. An alternative definition of "acid number" (sometimes used elsewhere) is the milliequivalents of potassium hydroxide required to neutralize the acidic groups on that polymer. If an "alternative" acid number is observed, it is converted to "acid number" as defined herein by multiplying the "alternative" acid number by 56.1.

A "polymer," as used herein and as defined by FW Billmeyer, JR. in Textbook of Polymer Science, second edition, 1971, is a relatively large molecule made up of the reaction products of smaller chemical repeat units. Polymers may have structures that are linear, branched, star shaped, looped, hyperbranched, crosslinked, or a combination thereof; polymers may have a single type of repeat unit ("homopolymers") or they may have more than one type of repeat unit ("copolymers"). Copolymers may have the various types of repeat units arranged randomly, in sequence, in blocks, in other arrangements, or in any mixture or combination thereof.

As used herein "weight of polymer" means the dry weight of polymer.

Molecules that can react with each other to form the repeat units of a polymer are known herein as "monomers."

One example of a class of monomers that are useful in the present invention are, for example, ethylenically unsaturated monomers (i.e., monomers that have at least one carbon-carbon double bond). Among such monomers are, for example, vinyl monomers, which are molecules that have at least one vinyl group (i.e.,

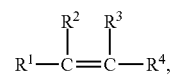

where each of $R^1$, $R^2$, $R^3$, and $R^4$ is, independently, a hydrogen, a halogen, an aliphatic group (such as, for example, an alkyl group), a substituted aliphatic group, an aryl group, a substituted aryl group, another substituted or unsubstituted organic group, or any combination thereof.

Some suitable vinyl monomers include, for example, styrene, substituted styrenes, dienes, ethylene, ethylene derivatives, and mixtures thereof. Ethylene derivatives include, for example, unsubstituted or substituted versions of the following: ethenyl esters of substituted or unsubstituted alkanoic acids (including, for example, vinyl acetate and vinyl neodecanoate), acrylonitrile, (meth)acrylic acids, (meth)acrylates, (meth)acrylamides, vinyl chloride, halogenated alkenes, and mixtures thereof. As used herein, "(meth)acrylic" means acrylic or methacrylic; "(meth)acrylate" means acrylate or methacrylate; and "(meth)acrylamide" means acrylamide or methacrylamide. "Substituted" means having at least one attached chemical group such as, for example, alkyl group, alkenyl group, vinyl group, hydroxyl group, carboxylic acid group, other functional groups, and combinations thereof. Suitable substituted monomers include, for example, monomers with more than one carbon-carbon double bond, monomers with hydroxyl groups, monomers with alkylene oxide chains of two or more units, monomers with other functional groups, and monomers with combinations of functional groups.

A polymer that is made by polymerizing a certain monomer, either alone or with other monomers, is said herein to include that monomer as a polymerized unit.

A chemical group that is part of a polymer is said herein to be "pendant" if it is covalently attached to the polymer but is not part of the backbone of the polymer chain.

As used herein, a "solvent" is a material that is liquid at 25° C.; that has boiling point, at 1 atmosphere pressure, of greater than 25° C.; and that is capable of dissolving a polymer of the present invention. A polymer is herein considered dissolved in a solvent if individual polymer chains are in intimate contact with the solvent. Individual dissolved polymer chains may be linear or branched. In typical solutions, each polymer chain is in a random coil configuration or a close approximation thereof. A polymer solution will not settle or form a separate phase upon standing for at least 5 days at 23° C.

A solvent may be a pure substance or it may contain plural substances dissolved in each other. For example, a solvent may contain two or more miscible liquids. Material that is solid at 25° C. is not considered to be part of the solvent, whether or not it is dissolved in liquid. As used herein, a solvent is "aqueous" if the solvent contains 50% or more water by weight based on the weight of the solvent. All other solvents are considered herein to be non-aqueous.

As used herein, when a ratio is said to be "X:1 or higher (or lower)" it is meant that the ratio has value of Y:1, where Y is equal to X or is higher (or lower).

As used herein, a heterocycle is a cyclic organic radical in which at least one member of the ring is a nitrogen atom, an oxygen atom, or a sulfur atom.

Preferably, 50% or more by weight of the microbicide, based on the total weight of microbicide, is not covalently bound to any polymer. The amount of microbicide that is not covalently bound to any polymer is, by weight based on the total weight of microbicide, more preferably 75% or more; more preferably 90% or more; more preferably 99% or more; more preferably 100%.

Preferably, the molecular weight of the microbicide of the present invention is 10,000 or less; more preferably 5000 or less; more preferably 1,500 or less; more preferably 750 or less.

Preferred are coating compositions in which no microbicide is present that has molecular weight greater than 10,000. More preferred are coating compositions in which no microbicide is present that has molecular weight greater than 1,500.

Any microbicide is suitable for use in the present invention. Suitable microbicides include, for example, quaternary ammonium microbicides, phenolic microbicides, chlorine and bromine oxidizing microbicides, organosulfur microbicides, heterocyclic microbicides, non-quaternary nitrogen-containing microbicides, other microbicides, and mixtures thereof.

Suitable quaternary ammonium microbicides include, for example, alkyl pyridinium compounds and compounds in which one or more trialkoxysilane-substituted alkyl group is attached to the quaternary nitrogen.

Preferred quaternary ammonium microbicides are those in which one or more of the groups attached to the quaternary nitrogen atom is an alkyl group with 8 or more carbon atoms. Suitable quaternary ammonium microbicides may have any counter ion. Preferred counter ions are halide ion; more preferred are bromide or chloride ion. The most preferred quaternary ammonium microbicides have chloride counter ion.

Also among the preferred quaternary ammonium microbicides are compounds in which a quaternary nitrogen atom is attached to two or more short alkyl groups, one or more long alkyl group, and, optionally, one benzyl group. Short alkyl groups have three or fewer carbon atoms; preferably two or fewer carbon atoms; preferably one carbon atom. Long alkyl groups have 8 or more carbon atoms. The benzyl group, if present, may be unsubstituted or substituted. Preferred substituted benzyl groups include, for example, benzyl groups with one, two, or three halogen atoms attached to the benzene ring; and benzyl groups with one or more alkyl groups (such as, for example, an ethyl group) attached to the benzene ring.

Preferred quaternary ammonium compounds are alkyl dimethyl benzyl ammonium compounds, dialkyl dimethyl ammonium compounds, alkyl trimethyl compounds, and mixtures thereof.

Alkyl dimethyl benzyl ammonium chlorides are compounds in which the quaternary nitrogen is attached to one benzyl group (which may be substituted or unsubstituted), two methyl groups, and one long alkyl group. One suitable alkyl dimethyl benzyl ammonium chloride is alkyl dimethyl ethylbenzyl ammonium chloride. Dialkyl dimethyl ammonium compounds are compounds in which the quaternary nitrogen is attached to two long alkyl groups and two methyl groups. Alkyl trimethyl ammonium compounds are compounds in which the quaternary nitrogen is attached to one long alkyl group and three methyl groups.

When an ammonium compound is described herein as having "one (or two) long alkyl group(s)" attached to the quaternary nitrogen, it is contemplated that the compound so described may exist as a mixture of compounds having various long alkyl groups. Preferred alkyl dimethyl benzyl ammonium chloride compounds are mixtures that include alkyl dimethyl benzyl ammonium chlorides in which the long alkyl group has any even number of carbon atoms from 12 to 18. Preferred dialkyl dimethyl ammonium chloride compounds are mixtures that include dialkyl dimethyl ammonium chlorides in which at least one of the two long alkyl group has 8 carbon atoms or 10 carbon atoms.

Among phenolic microbicides, preferred are those in which a ring hydrogen on a phenol molecule is substituted with one or more halogen atom, one or more phenyl group, one or more benzyl group, one or more phenoxy group, one or more chlorophenoxy group, one or more dichlorophenoxy group, one or more alkyl group, or a combination thereof. Preferred phenolic microbicides include 2-phenyl-4-chlorophenol, o-phenylphenol, pentachlorophenol, 2(2',4'-dichlorophenoxy)-5-chlorophenol, 4-chloro-3-methylphenol, and mixtures thereof. Among phenolic microbicides, the most preferred is o-phenyl phenol.

Biguanide radical is the radical with the structure

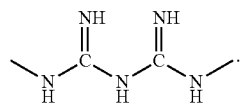

As used herein, a polymeric biguanide is a compound that contains two or more biguanide radicals. In a polymeric biguanide, the biguanide radicals may, for example, be connected to each other via a linking group. The compound "biguanide" is the biguanide radical, capped with two hydrogens.

Preferably, the composition of the present invention contains one or more quaternary ammonium microbicides, one or more phenolic microbicides, or a mixture thereof. Preferably, every microbicide present in the composition of the present invention is either a phenolic microbicide or quaternary ammonium microbicide. Preferred compositions of the present invention contain one or more quaternary ammonium microbicide. Preferably, every microbicide present in the composition of the present invention is a quaternary ammonium microbicide.

The preferred minimum amount of microbicide in the composition of the present invention is, by weight based on the total weight of the composition, 0.01%; more preferably 0.02%; more preferably 0.05%; more preferably 0.1%; more preferably 0.2%. Independently, the preferred maximum amount of microbicide in the composition of the present invention is, by weight based on the total weight of the composition, 15%; more preferably 10%; more preferably 8%.

The present invention involves the use of one or more soluble polymer that is a non-anionic polymer. The non-anionic polymer of the present invention has acid number less than 10. Preferred polymers have acid number less than 5; more preferred have acid number less than 1; more preferred have acid number less than 0.5. The non-anionic polymer of the present invention either has no anionic groups or else has few enough anionic groups so that the acid number of the polymer meets the criteria stated above. Any polymer that has acid number of 10 or greater is referred to herein as an "anionic" polymer.

Among embodiments in which anionic groups are present in a small amount in a non-anionic polymer, the anionic groups may have any origin. For example, the polymerization process that produced the non-anionic polymer may have involved a small amount of a chain transfer agent that contains a carboxyl group, and that carboxyl group may have become attached to the polymer chain. When such chain transfer agents are used at normal amounts, the resulting polymer will have acid number that is less than 10. For another example, if a polymer that contains polymerized units of acrylamide were exposed to aggressive forcing conditions (such as extended time periods at elevated temperature and/or high pH) some of the amide groups could possibly be converted to carboxyl groups by hydrolysis. Such polymers will have acid number of less than 10 unless exposed for long periods to aggressive forcing conditions.

The statement that the non-anionic polymer has no anionic groups means herein that, in the composition of the present invention, the polymer has no groups that are in an anionic state when the composition of the present invention has pH of 7 or higher. Preferably, the polymer has no groups that are in an anionic state when the composition of the present invention has pH of 6 or higher; more preferably 5 or higher; more preferably 3 or higher; more preferably 2 or higher. Independently, preferred polymers of the present invention have no pendant carboxylic acid groups. More preferably, polymers of the present invention have no pendant carboxylic acid groups and no pendant sulfonic acid groups. Preferred polymers of the present invention have no pendant acid groups of any kind. Preferably, every polymer in the composition of the present invention is a non-anionic polymer. More preferably, every polymer in the composition of the present invention has no pendant acid groups of any kind.

Preferably, the present invention involves the use of one or more nonionic soluble polymer. The statement that the polymer is nonionic means herein that, in the composition of the present invention, the polymer either does not have functional groups that are ionic or, if any ionic groups are present, the polymer meets the criteria regarding acid number stated herein above. Preferably, the polymer has no groups that are in an ionic state when the composition of the present invention has pH of 7 or higher; more preferably 6 or higher; more preferably 5 or higher; more preferably 3 or higher. Independently, it is preferable that the polymer has no groups that are in an ionic state when the composition of the present invention has pH of 9 or lower; more preferably 10 or lower; more preferably 12 or lower.

Preferably, a polymer of the present invention is a vinyl polymer. As used herein, a vinyl polymer is a polymer formed from vinyl monomers by polymerization reaction among carbon-carbon double bonds to form the polymer backbone. Preferred vinyl polymers are made by free-radical polymerization. Preferably, the polymer of the present invention contains no carbon-oxygen bond in the polymer chain (independent of whether there are carbon-oxygen bonds in any of the pendant groups). Preferably, every polymer in the composition of the present invention is a vinyl polymer.

The polymer of the present invention has polymerized units of acrylamide. Acrylamide has the structure I:

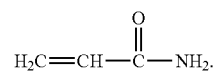

The preferred minimum amount of polymerized units of acrylamide in the polymer is, by weight based on the weight of the polymer, 5%; more preferably 15%; more preferably 50% or more; more preferably 60% or more; more preferably 70% or more; more preferably 80% or more.

Preferably, a polymer is used that contains polymerized units of one or more "additional monomer" (i.e., monomer in addition to acrylamide). It is contemplated that any additional monomer that is used will be chosen so that the polymer of the present invention will be soluble and will be non-anionic.

Suitable additional monomers include, for example, ethenyl esters of substituted and unsubstituted alkanoic acids, substituted and unsubstituted alkyl esters of (meth)acrylic acid, and mixtures thereof.

Preferred additional monomers include acrylamide-variant monomers, monomers that are not acrylamide-variant and that contain a heterocycle, water-soluble substituted alkyl esters of (meth)acrylic acid, and mixtures thereof.

A monomer is considered water-soluble herein if it is soluble in water in an amount, by weight of monomer based on the weight of water, of 0.1% or more. Preferably, if a water-soluble monomer is used, that water-soluble monomer is soluble in water in an amount, by weight of monomer based on the weight of water, of 0.3% or more; more preferably 1% or more; more preferably 3% or more.

Acrylamide-variant monomers have the structure II:

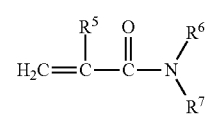

where one or more of $R^5$, $R^6$, and $R^7$ is not hydrogen. $R^5$ is hydrogen or methyl. $R^6$ and $R^7$ are, independently of each other, hydrogen, unsubstituted alkyl, or substituted alkyl. Preferred alkyl groups have 1 to 12 carbon atoms. Suitable alkyl groups may be linear, branched, cyclic, or a combination thereof. Suitable substituents on the alkyl group, when present, may be, for example, amine groups, alkylamine groups, hydroxyl groups, halogen atoms, or combinations thereof.

Preferred acrylamide-variant monomers are those in group A and those in group B. Group A monomers have structure II in which $R^5$ is hydrogen, $R^6$ is hydrogen, and $R^7$ is an unsubstituted alkyl group. Among group A monomers, preferably, $R^7$ is an unsubstituted alkyl group with 2 to 6 carbon atoms; more preferably, $R^7$ is isopropyl or tert-butyl. Group B monomers have structure II in which $R^5$ is hydrogen, $R^6$ is an unsubstituted alkyl group, and $R^7$ is an unsubstituted alkyl group identical to $R^6$. Among Group B monomers, preferably, $R^6$ is methyl. Group A monomers are preferred.

Among polymers that contain polymerized units of one or more acrylamide-variant monomer, the preferred minimum total amount of acrylamide-variant monomers is, by weight based on the weight of that polymer, 1%; more preferably 2%; more preferably 5%; more preferably 8%; more preferably 10% or more. Independently, the preferred maximum total amount of acrylamide-variant monomers is, by weight based on the weight of that polymer, 50%; more preferably 35%; more preferably 25%.

Another suitable class of additional monomers (known herein as "heterocycle monomers") is monomers that are not acrylamide-variant monomers and that have one or more pendant heterocycle. As used herein, a heterocycle is pendant when it is covalently attached to the monomer in such a way that the heterocycle will not participate in the polymerization reaction. Each suitable heterocycle has one or more member of the heterocycle ring that is one or more nitrogen, or one or more oxygen, or one or more sulfur, or a combination thereof.

Preferred are polymers that contain no polymerized units of heterocycle monomers or that contain polymerized units of heterocycle monomers in the amount of less than 5% by weight based on the weight of the polymer. More preferred are polymers that contain no polymerized units of heterocycle monomers.

Preferred polymers contain polymerized units of one or more additional monomer. More preferred are polymers that contain polymerized units of one or more group A monomers or one or more heterocycle monomers or a mixture thereof. More preferred are polymers that contain polymerized units of one or more group A monomers. More preferred are polymers that contain polymerized units of one or more group A monomers and that have no polymerized unit of any monomer with one or more pendant heterocycle. More preferred are polymers that contain polymerized units of one or more group A monomers and acrylamide.

In some embodiments, a polymer is used that has polymerized units of one or more multifunctional monomer. In vinyl polymers, multifunctional monomers are those that have two or more carbon-carbon double bonds capable of participating in vinyl polymerization. Preferred are polymers with no polymerized units of multifunctional monomer.

Preferred are compositions of the present invention in which every polymer that is used is a polymer that has no polymerized unit of any monomer with one or more pendant heterocycle. Preferred are compositions of the present invention in which every polymer that is used is a polymer in which every polymerized unit is selected from acrylamide, one or more group A monomers, and mixtures thereof.

Preferred are polymers in which every polymerized unit is a nonionic monomer.

Preferred are coating compositions that either contain no anionic polymer or, if any anionic polymer is present, have weight ratio of all anionic polymers to all non-anionic polymers of 0.1:1 or less; more preferred 0.01:1 or less. More preferred are coating compositions that contain no anionic polymer. More preferred are coating compositions that contain no polymer that has any anionic group.

Preferred are coating compositions that contain one or more nonionic polymer and that either contain no polymer that has any ionic group or, if any polymer having an ionic group is present, have weight ratio of all polymers containing ionic groups to all polymers having no ionic groups of 0.1:0 or less; more preferred 0.01:1 or less. More preferred are coating compositions that contain one or more nonionic polymer and that contain no polymer that has any ionic group.

Preferably, in the coating composition of the present invention, the amount of polymer, by weight based on the total weight of the composition, is 0.01% or more; more preferably 0.02% or more; more preferably 0.05% or more; more preferably 0.2% or more; more preferably 0.5% or more. Independently, preferably, the amount of polymer, by weight based on the total weight of the composition, is 10% or less; more preferably 5% or less; more preferably 2.5% or less.

Independent of the amount of polymer used, in the coating composition of the present invention, the preferred weight ratio of microbicide to polymer is 0.01:1 or higher; more preferably 0.02:1 or higher; more preferably 0.05:1 or higher; more preferably 0.1:1 or higher. Independently, preferably, the weight ratio of microbicide to polymer is 8:1 or lower; more preferably 5:1 or lower; more preferably 2:1 or lower; more preferably 1:1 or lower; more preferably 0.5:1 or lower.

In addition to the coating compositions described herein above, also envisioned are concentrate compositions. Concentrate compositions have the same ingredients as coating compositions. In concentrate compositions, the ratios of the non-solvent ingredients to each other are the same as in coating compositions, but the concentration of polymer in a concentrate composition is 10 to 20 times higher than in a coating composition. Non-solvent ingredients are every ingredient other than solvent.

The practice of the present invention involves the use of solvent. Any solvent is suitable. Preferably, the solvent is aqueous. Preferably, the amount of water in the solvent, by weight based on the weight of solvent is 75% or more, more preferably 85% or more; more preferably 95% or more; more preferably 99% or more. Preferably, the solvent contains one or more alkyl alcohol. Preferred alkyl alcohols are, those with 10 or fewer carbon atoms; more preferably 6 or fewer carbon atoms; more preferably 4 or fewer carbon atoms; more preferably 3 or fewer carbon atoms. Independently, preferred alkyl alcohols are those with 2 or more carbon atoms. Preferably, ethanol is used, either alone or mixed with water.

It is contemplated that one or more additional alcohol may be present in the coating composition of the present invention in small amounts. Such additional alcohol may possibly have been introduced as an impurity that was present in a raw material and/or as a carry-over solvent from the polymerization process. In preferred embodiments, in the coating composition of the present invention, the amount of alkyl alcohol other than ethanol is, by weight based on the weight of soluble polymer, 1% or less, more preferably 0.3% or less, more preferably 0.1% or less.

Preferred compositions of the present invention contain one or more wetting agents. Suitable wetting agents include, for example, nonionic surfactants, anionic surfactants, cationic surfactants, amphoteric surfactants, fluorosurfactants, and silicone surfactants. Preferred wetting agents are anionic surfactants, fluorosurfactants, and silicone surfactants. More preferred are anionic surfactants. Suitable anionic surfactants include, for example, compounds that are alkali-metal salts of sulfosuccinate, sulfate or sulfonate compounds and that contain one or more fatty chain. As used herein, a fatty chain is a hydrocarbon chain that contains 6 or more carbon atoms. Preferred anionic surfactants are alkali-metal salts of sulfonate compounds that contain one or more fatty chain.

Some suitable compositions of the present invention contain one or more chelating agent. As used herein, a "chelating agent" is a compound that contains two or more electron-donor atoms that are capable of forming coordinate bonds with a metal atom, and a single molecule of the chelating agent is capable of forming two or more coordinate bonds with a single metal atom. Some suitable chelating agents are, for example, aminocarboxylic acids and their salts; hydroxycarboxylic acids and their salts; amino acid chelants; heterocyclic chelants; amine chelants; organophosphonate chelants, beta-diketone chelants; and mixtures thereof. Suitable amino acid chelants include aminoalcohols, aminophenols, glutamic acid and its salts, N,N-diacetic acid and its salts, and mixtures thereof. Suitable amine chelants include polyamines, Shiff bases, and mixtures thereof. Preferred chelating agents include one or more aminocarboxylic acids, one or more hydroxycarboxylic acids, one or more heterocyclic chelant, or a mixture thereof. Preferred aminocarboxylic acids and their salts include the acid and salt forms of ethylenediaminetetraacetic acid (EDTA), hydroxyethylethylenediaminetriacetic acid (HEDTA), diethylenetriaminepentaacetic acid (DTPA), nitrilotriacetic acid (NTA), N-dihydroxyethylglycine (2-HxG), ethylenebis(hydroxyphenylglycine) (EHPG), and mixtures thereof. Preferred hydroxycarboxylic acids and their salts include the acid and salt forms of tartaric acid, citric acid, gluconic acid, 5-sulfosalicylic acid, sodium glucoheptonate; sodium diethanolglyicine (DEG); disodium ethanoldiglycine (HEIDA), iminodisuccinic acid (ICS), and mixtures thereof. Preferred heterocyclic chelants include aromatic heterocyclic bases, oximes, and mixtures thereof. Preferred oximes include dimethylglyoxime, salicylaldoxime, and mixtures thereof. Preferred are aminocarboxylic acids. More preferred is EDTA.

When anionic surfactant is used, preferably the weight ratio of polymer to anionic surfactant is 40:1 or greater; more preferably 55:1 or greater; more preferably 70:1 or greater. When anionic surfactant is used, preferably the weight ratio of polymer to anionic surfactant is 500:1 or less; more preferably 250:1 or less.

When anionic surfactant and quaternary ammonium biocide are both used, preferably the weight ratio of quaternary ammonium biocide to anionic surfactant is 5:1 or greater; more preferably 9:1 or greater; more preferably 12:1 or greater. When anionic surfactant and quaternary ammonium biocide are both used, preferably the weight ratio of quaternary ammonium biocide to anionic surfactant is 200:1 or less; more preferably 100:1 or less.

The composition of the present invention is a liquid coating composition. It is contemplated that one preferred method of making use of the composition of the present invention is to apply a layer of the composition to a substrate and dry the composition or allow it to dry. The act of applying a layer of the composition to a substrate and then drying it or allowing it to dry is known herein as "coating" the substrate. It is contemplated that, as the solvent evaporates, the composition will form a film on the substrate. The dried layer of the composition is known herein as "a coating." Drying is preferably done at 18° C. or higher.

Composition may be applied to a substrate by any method, including methods conducted by hand and methods conducted by machine and combinations thereof. For example, composition may be applied by spraying (pump, aerosol, pressure, etc.), pouring, spreading, metering (for example, with a rod or bar), mopping, wiping, brushing, dipping, mechanical application, other application methods, or combination thereof. It is contemplated that the composition could be altered (for example, by adjusting solids level, adding one or more adjuvants, etc.) so that the coating composition would have the proper properties for the chosen method of applying to substrate.

Suitable adjuvants include, for example, rheology modifiers, fragrances, structurants, reactive resins, colorants, acids or bases, buffers, surfactants, solvents, and mixtures thereof.

Some possible adjuvants include crosslinkers. Crosslinkers are compounds that are not polymers or microbicides suitable for the present invention and that have two or more reactive groups capable of reacting with reactive groups attached to a polymer. Common crosslinkers include isocyanates, aziridines, carbodiimides, and melamines. Preferred are compositions that contain no isocyanates, no aziridines, no carbodiimides, and no melamines. More preferred are compositions that contain no crosslinkers.

Some suitable reactive resins include, for example, epoxy resins. Epoxy resins may be used, for example, when the polymer of the present invention contains polymerized units of a pendant heterocycle, when that heterocycle is capable of reacting with the epoxy group of the epoxy resin. Preferred are compositions of the present invention in which no epoxy resin is present.

Preferably, after a layer of composition of the present invention is applied to a substrate and dried, the resulting coating is not tacky. One method of assessing tack is the Probe Tack Test, ASTM D 2979-01 (published by the American Society of Testing and Materials, West Conshohocken, Pa., USA). A dry coating that requires 1 N or less force to remove the probe is considered herein to be not tacky.

Another method of measuring tack is to touch the surface of the dry coating with a gloved finger. A coating is considered tacky if noticeable force is required to remove the glove from the surface of the coating.

A dry layer of a coating that is not tacky by any one or more of the above criteria is considered herein to be not tacky.

It is expected that coatings of the present invention have microbicidal activity. It is further expected that coatings of the present invention will maintain that microbicidal activity under normal use or after being subjected to wearing operations such as, for example, EPA Protocol #01-1A, "Protocol for Residual Self-Sanitizing Activity of Dried Chemical Residues on Hard, Non-Porous Surfaces."

Preferably, the coating composition of the present invention contains little or no polyurethane. More preferably, the amount of polyurethane in the coating composition of the present invention is either zero or, if not zero, is, by weight of dry polyurethane based on the weight of the coating composition, 0.01% or less; more preferably 0.001% or less. More preferably, there is no polyurethane in the coating composition of the present invention.

The coating composition of the present invention may be packaged in any form. For example, the coating composition of the present invention may be an aerosol spray; or a pump spray; or a liquid suitable for applying to a substrate with an applicator such as, for example, a brush, roller, or mop; or a concentrated liquid that, when diluted, will be suitable for applying to a substrate with an applicator such as, for example, a brush, roller, or mop. For another example, the coating composition of the present invention may be absorbed into a wet wipe (i.e., a piece of paper, woven fabric, or non-woven fabric that carries some of the coating composition of the present invention in wet form).

The coating composition of the present invention may be put to use by coating any substrate. Some suitable substrates include, for example, countertops, mirrors, sinks, toilets, light switches, doorknobs, walls, floors, ceilings, partitions, railings, computer screens, keyboards, instruments, etc. Suitable substrates may be found in various settings including, for example, food preparation areas, households, industrial settings, architectural settings, medical settings, sinks, toilets, etc. Substrates may be made of any material; some suitable substrate compositions include, for example, plastic (including, for example, laminates and wall coverings), Formica, metal, glass, ceramic tile, paper (such as, for example, wallpaper), fabric, finished or unfinished wood, etc.

It is to be understood that for purposes of the present specification and claims that each operation disclosed herein is performed at 25° C. unless otherwise specified.

Preferred liquid coating compositions of the present invention are described herein as "clear." Such compositions will be clear unless one or more colorants (i.e., pigments, including white pigments, or dyes or other ingredients intended to provide color and/or opacity) are added. Similarly, the dried coatings made from such compositions will be clear unless one or more colorants are added. Compositions of the present invention to which one or more colorants have been added are considered to be embodiments of the present invention; such coating compositions or the coatings made from them will have improved appearance because of the clarity of the non-colorant portion of the composition.

Coatings made from the coating compositions of the present invention are preferably removable using water-based cleaners. That is, while such coatings preferably pass the tests described herein below that include wear cycles, it is desirable that the same coating be removable using water-based cleaners and moderate mechanical force. Water-based cleaners are liquid products that contain 25% or more water by weight, based on the weight of the liquid product. Water-based cleaners include water and include liquids that contain ammonia, include one or more surfactant, or include a combination thereof. Moderate mechanical force is the force that can be exerted by hand using a cloth, sponge, cleaning pad, or other hand-held device for applying cleaner to a surface.

EXAMPLES

Coating Compositions: Each polymer was made by solution polymerization in a polymerization solvent. The polymer solution thus made was then added to a coating solvent to make each of the coating compositions shown below.

Microbicidal activity of the coating compositions was evaluated by two test methods: (1) AOAC method 961.01, "Germicidal Spray Products," published by AOAC International, Gaithersburg, Md., USA, and (2) "Protocol #01-1A: Protocol for Residual Self-Sanitizing Activity of Dried Chemical Residues on Hard, Non-Porous Surfaces," (herein called "EPA Protocol") published by the U.S. Environmental Protection Agency, 1200 Pennsylvania Avenue, N.W., Washington, D.C. 20460, USA, available at http://www.epa.gov/oppad001/cloroxpcol_final.pdf.

In the Germicidal Spray Products test, a sterile glass slide was inoculated with test organism and air dried. Disinfectant product was applied. Contact time was 5 minutes. Sample was neutralized, and incubated for 48 hours at 37° C. and examined. "Pass" meant no growth; "Fail" meant growth. 5% organic soil load (fetal bovine serum) was included in the inoculation. For each combination of sample and microorganism, 2 slides were run. 5% organic soil load (fetal bovine serum) was included in each inoculation. This test evaluates the biocidal properties of the formulation itself.

The EPA protocol as reported here was conducted as follows. A sample surface of size 2.5 cm×2.5 cm (1 inch×1 inch) was sterilized and then inoculated with a microorganism, allowing the inoculum to dry; 50 microliters of the coating composition of interest was applied to the surface; and the coating composition was allowed to dry. The surface was exposed to one wear cycle (forward and back) with a Gardner Washability and Wear Tester boat wrapped with polyurethane foam and a dry cotton cloth. The surface was then re-inoculated with the test microorganism and allowed to dry; the surface was then exposed to one wear cycle with the Gardener wear test boat described above, wrapped with a moist cloth; and the surface was again re-inoculated with the test microorganism and allowed to dry. The series of dry and moist wear cycles (including reinoculations) was performed 5 times and then the wear steps were completed using either variation I or variation II. This test evaluates the biocidal properties of a film formed from the formulation.

In variation, I, no further re-inoculations were performed. The surface was then exposed to further wear cycles, starting with a moist cloth and alternating wear cycles with moist cloth with wear cycles with dry cloth, until a total of 12 wear cycles were performed in the entire test procedure.

In variation II, the wear steps were performed as in variation I, and the surface was re-inoculated with the test microorganism after each wear step, for a total of 11 re-inoculations in the entire test procedure.

At least 24 hours after applying the coating composition of interest, the microbicide was neutralized, any remaining microorganisms were collected and cultured on agar plates, which were incubated for 48 hours, and the number of surviving microorganisms was observed. Multiple plates were tested for the control treatment and for each of the tested coating compositions. The results are reported as "% reduction," which is the difference of the geometric mean of the number of surviving organisms in the control samples and the geometric mean of the number of surviving organisms in the test samples, multiplied by 100 and divided by the geometric mean of the number of surviving organisms in the control samples. Percent reduction of greater than 99.9% is considered passing.

The microorganism used was *Staphylococcus aureus* (ATCC#6538) or *Klebsiella pneumoniae* (ATCC#4352) or *Esherichia coli* (ATCC#8739) or *Pseudomonas aeruginosa* (ATCC#15442) or *Acinetobacter baumannii* (ATCC#19606) or *Salmonella choleraesuis* (ATCC#10708).

The Abbreviations used below are as follows:
tBAM=N-tert-butyl acrylamide
AmCl=ammonium chloride
NVP=1-vinyl-2-pyrrolidinone
B1=BTC™ 885 biocide (Stepan Co.), blend of n-Alkyl Dimethyl Benzyl AmCl (CAS#68424-85-1) and Dialkyl Dimethyl AmCl (CAS#68424-95-3). Composition:
  20% n-Alkyl (50% C14, 40% C12, 10% C16) Dimethyl Benzyl AmCl
  15% n-Octyl Decyl Dimethyl AmCl
  7.5% Di-n-Octyl Dimethyl AmCl
  7.5% Di-n-Decyl Dimethyl AmCl
B2=BTC™ 2125M biocide (Stepan Company), blend of n-Alkyl Dimethyl Benzyl AmCl (CAS#6839-01-5) and n-Alkyl Dimethyl Ethylbenzyl AmCl (CAS#68956-79-6). Composition:
  25% n-Alkyl (60% C14, 30% C16, 5% C12, 5% C18) Dimethyl Benzyl AmCl
  25% n-Alkyl (68% C12, 32% C14) Dimethyl Ethylbenzyl AmCl
PHMB=Polyhexamethylene biguanide (Arch Chemicals, Inc.)
RH=relative humidity
S1=Triton™ GR-5M sulfosuccinate surfactant, (Dow Chemical Co.)

S2=Chemguard™ S-559 perfluoroalkyl substituted polyether surfactant (Chemguard)

S3=Sodium Dodecyl Sulfonate (Sino Pharm Chemical Reagent Co.)

S4=ChemGuard™ S550 perfluoroalkyl substituted polyether surfactant (Chemguard)

EDTA=ethylenediamine tetraacetic acid (Sino Pharm Chemical Reagent Co.)

Example 1

Polymer Compositions Tested

| Polymer No. | Composition[1] |
|---|---|
| P01 | 100% Acrylamide |
| P02 | 5 tBAM/95 Acrylamide |
| P03 | 10 tBAM/90 Acrylamide |
| P04 | 15 tBAM/85 Acrylamide |
| P05 | 25 tBAM/75 Acrylamide |
| P06 | 15 tBAM/10 NVP/75 Acrylamide |
| P07 | 25 N-Isopropylacrylamide/75 Acrylamide |
| P08 | 35 acrylamide/65 vinyl pyrrolidone |
| P09 | 50 acrylamide/50 vinyl pyrrolidone |
| P10 | 65 acrylamide/35 vinyl pyrrolidone |
| P11 | 75 acrylamide/25 vinyl pyrrolidone |
| P12C[2] | 100 N,N-dimethylacrylamide |
| P13 | 75 acrylamide/25 dimethylacrylamide |

Note 1:
percent by weight of each monomer, based on the total weight of monomer
Note 2:
comparative example

Example 2

Preparation of Formulations

"Ready to use Formulations" were made as follows. Polymer in the form of an aqueous solution (approximately 30% solids) was added to the mixing vessel. Deionized water was added and stirred. The pH was adjusted to approximately 8 with a solution of NaOH in water (1% by weight). Additives (if any) were added and stirred. Biocide (in the form of an aqueous solution) was added and stirred. The amounts of each material was chosen to give the concentrations shown in the examples below.

Example 3

Physical Evaluation of Films

Ready to use formulations were prepared as in Example 2. Films were prepared by transfer of 100 microliter of the formulation to a 25.4 mm (1 inch)×50.8 mm (2 inch) glass slide. The liquid was spread across the surface and allowed to dry under conditions of ambient temperature (20° C. to 25° C.) and humidity (10% to 50% RH). After drying, each film was evaluated visually for film clarity or haziness. Film tackiness or greasiness was evaluated by touch with a gloved finger. The desirable biocide-containing films are clear upon drying, with no tackiness or greasy residue.

| Polymer | wt % Polymer[1] | Biocide | ppm[2] active Biocide | Film Clarity | Tacky or Greasy? |
|---|---|---|---|---|---|
| P2 | 1.5 | B1 | 2500 | hazy | none |
| P1 | 1.5 | B2 | 3000 | hazy | none |
| P2 | 1.5 | B1 | 2500 | hazy | none |
| P3 | 1.5 | B1 | 2500 | clear | none |
| P4 | 1.5 | PHMB | 2500 | clear | none |
| P4 | 1.5 | B1 | 2500 | clear | none |
|  |  | PHMB | 2500 |  |  |
| P4 | 1.5 | B1 | 3000 | clear | none |
| P4 | 1.5 | B2 | 5000 | clear | none |
| P5 | 1.5 | B1 | 2500 | clear | none |
| P6 | 2.0 | B1 | 3000 | clear | none |
| P8 | 1.5 | B1 | 3000 | hazy | none |
| P11 | 2.0 | B1 | 3000 | hazy | none |
| P11 | 1.5 | B2 | 3000 | hazy | none |
| P11 | 2.0 | B2 | 3000 | hazy | none |
| P9 | 2.0 | B1 | 3000 | hazy | none |
| P10 | 2.0 | B1 | 3000 | hazy | none |
| P12C[3] | 2.0 | B1 | 3000 | hazy | greasy |
| P13 | 2.0 | B1 | 3000 | hazy | none |
| P7 | 2.0 | B1 | 3000 | clear | none |
| none[3] |  | B1 | 3000 | hazy | tacky, greasy |
| none[3] |  | B2 | 5000 | hazy | tacky, greasy |
| none[3] |  | PHMB | 5000 | hazy | slight tack |
| none[3] |  | PHMB | 2500 | hazy | tacky, greasy |
|  |  | B1 | 2500 |  |  |

Note 1:
weight percent of polymer solids, based on the total weight of the formulation.
Note 2:
parts by weight of active biocide, based on the total weight of the formulation
Note 3:
Comparative examples Films with no polymer and films with comparative polymer were greasy and/or tacky. Films with polymers of the present invention were neither tacky nor greasy. Films with polymers having 10% or more alkyl acrylamide were clear, while others were hazy.

Example 4

Biocidal Activity of Formulations: AOAC Germicidal Spray Products Method

In the following samples, the biocide was B1, and the wt % polymer was 2.0%. This method does not involve abrasion. Ready to use formulations were made as in Example 2.

| polymer | ppm Biocide | S. aureus | K. pneumoniae | P. aeruginosa |
|---|---|---|---|---|
| P6 | 0 | FAIL | FAIL | FAIL |
| P4 | 0 | FAIL | FAIL | FAIL |
| none | 3000 | PASS | PASS | PASS |
| P6 | 2500 | PASS | PASS | PASS |
| P4 | 2500 | PASS | PASS | PASS |
| P4 | 3000 | PASS | PASS | PASS |

Example 5

Evaluation of Film Residual Biocidal Activity: EPA Protocol

Ready to use formulations were made as in Example 2, and films were made as in the EPA Protocol.
5-1. Polymer P7+Biocide B1–Variation in Polymer Dosage:
test conditions: Variation I, 22.8° C., 71% RH during testing (slides dried at 50% RH), biocide concentration was 3000 ppm.

| wt % polymer | P. aeruginosa |
|---|---|
| 2.0 | >99.9 |
| 1.8 | >99.9 |
| 1.6 | >99.9 |
| 1.4 | >99.9 |
| 1.2 | >99.9 |
| 2.0 | >99.9[(4)] | note 4:
this sample was tested at 12 wears and 11 reinoculations (vs. standard of 5 reinoculations) using Variation II.

5-2. Polymer P6 and Polymer P4 and Biocide B1
test conditions: Variation I, 22° C., 35-54% RH

| polymer | wt % polymer | ppm Biocide | S. aureus[(4)] | K. pneumoniae[(4)] | P. aeruginosa |
|---|---|---|---|---|---|
| P6 | 1.5 | 2500 | >99.9 | >99.9 | >99.9 |
| P4 | 1.5 | 2500 | >99.9 | >99.9 | >99.9 |
| P4 | 2.0 | 2500 | not tested | not tested | >99.9 |
| P6 | 2.0 | 0 | FAIL[(5)] | −31.6 | 11.4 |
| P4 | 2.0 | 0 | FAIL[(5)] | 3.46 | 21.6 |
| none | 0 | 2500 | FAIL[(5)] | −56.5 | not tested |
| none | 0 | 3000 | not tested | not tested | 14.8 |

Note 4:
these samples were tested at 12 wears and 11 reinoculations (vs. standard of 5 reinoculations) using Variation II.
Note 5:
microorganisms were too numerous to count.

5-3. Acrylamide/Vinyl Pyrrolidone Polymers+Biocide B1 at 3000 ppm
Variation I, test conditions: 21° C., 50% RH; wt % polymer was 2.0%.

| polymer | P. aeruginosa |
|---|---|
| P8 | >99.9 |
| P11 | >99.9 |
| P9 | >99.9 |
| P10 | >99.9 |

5-44. Polymer P4+Biocide B1 Plus Additives
test conditions: Variation II, 22° C., 20% RH, mirrored stainless steel slides; Wt % of polymer was 1.5%; amount of biocide was 3000 ppm.

| additive | P. aeruginosa |
|---|---|
| 200 ppm of Triton ™ GR-5M sulfosuccinate surfactant, (Dow Chemical Co.) | >99.9 |
| 200 ppm of Chemguard ™ S-559 fluorosurfactant (Chemguard). | >99.9 |

Example 6

Wetting of Surface

The following formulations were made. Each formulation contained 0.3% B1 by weight based on the weight of the formulation. In addition to the ingredients shown, the remainder of each formulation was water. Formulation 6-1C is comparative. A rectangular layer of each formulation was drawn onto hard, flat surface. Immediately after creation of the layer, the layer was rectangular; each had an average width (W0). Each layer was observed after 5 minutes. If the layer was rectangular, the width (W5) is reported as a percentage (100*W5/W0).

| Formulation No. | P4 (%) | Surfactant | Surfactant (%) | Appearance after 5 min. |
|---|---|---|---|---|
| 6-1C | 0 | none | 0 | de-wetted[(1)] |
| 6-2 | 1.5 | none | 0 | de-wetted[(1)] |
| 6-3 | 1.5 | S3 | 0.02 | rectangular, width 100% |
| 6-4 | 1.5 | S1 | 0.02 | rectangular, width 100% |
| 6-5 | 1.5 | S4 | 0.02 | rectangular[(2)], width 80% |
| 6-6 | 1.5 | S2 | 0.02 | rectangular[(2)], width 66% |

Note 1:
perimeter has drawn in toward the center to form irregular shape or shapes.
Note 2:
sides of the rectangle were somewhat wavy; W5 was the estimated average width of the layer of the coating composition.

On this particular surface, the formulations with surfactant do not show the de-wetting phenomenon. The samples with anionic surfactant (6-3 and 6-4) perform better than the samples with nonionic surfactant (6-5 and 6-6).

Example 7

Storage Stability of Liquid Coating Compositions and Concentrates

A concentrate was made using B1, P4, and S3, with the ratios to each other the same as in formulation 6-3. The amount of water in the concentrate was lower than in formulation 6-3, so that the concentration of each ingredient other than water in the concentrate was 15 times higher than the concentration of that ingredient in formulation 6-3. Sealed vials of concentrate and of formulation 6-3 were stored at indoor ambient temperature (approximately 20° C.). All the samples appeared clear at the beginning and were still clear after 2 weeks.

Example 8

Effect of Polymer

Quaternary Ammonium Biocide Compound was Mixed with Anionic surfactant at concentrations described herein above as appropriate for the present invention. The result was hazy solution and deposition of material on the bottom of the container. It is considered that formulations like 6-3 and 6-4, if the polymer were omitted, would show such haze and/or deposition.

We claim:
1. A clear coating composition comprising
   (a) one or more microbicide,
   (b) one or more soluble polymer comprising acrylamide as polymerized units, wherein said polymer is non-anionic, and
   (c) solvent,
   wherein said polymer is dissolved in said solvent;
   further wherein the polymer is a copolymer selected from the group consisting of N-tert-butyl acrylamide/acrylamide and N-isopropylacrylamide/acrylamide.
2. The coating composition of claim 1, wherein said biocide comprises one or more biocide selected from the group consisting of one or more quaternary ammonium biocides, one or more phenol biocides, one or more biguanide biocides, and mixtures thereof.

3. The coating composition of claim 1, wherein said composition additionally comprises one or more wetting agent.

4. The coating composition of claim 1, wherein said composition additionally comprises one or more anionic surfactant.

5. The coating composition of claim 1, wherein said biocide comprises one or more quaternary ammonium biocides.

6. The coating composition of claim 1, wherein said biocide comprises one or more quaternary ammonium biocides, and wherein said composition additionally comprises one or more anionic surfactant.

7. The coating composition of claim 6, wherein the weight ratio of said quaternary ammonium biocide to said anionic surfactant is from 5:1 to 30:1.

8. A method of coating a substrate comprising applying a layer of the composition of claim 1 and drying said layer or allowing said layer to dry.

9. A coated substrate made by the method of claim 8.

* * * * *